US011747662B2

(12) United States Patent
Xue (10) Patent No.: US 11,747,662 B2
(45) Date of Patent: Sep. 5, 2023

(54) ELECTRONIC DEVICE AND WEARABLE DEVICE WITH ELASTOMERIC MEMBER

(71) Applicant: GUANGDONG OPPO MOBILE TELECOMMUNICATIONS CORP., LTD., Guangdong (CN)

(72) Inventor: Yuege Xue, Guangdong (CN)

(73) Assignee: GUANGDONG OPPO MOBILE TELECOMMUNICATIONS CORP., LTD., Dongguan (CN)

( * ) Notice: Subject to any disclaimer, the term of this patent is extended or adjusted under 35 U.S.C. 154(b) by 347 days.

(21) Appl. No.: 17/094,055

(22) Filed: Nov. 10, 2020

(65) Prior Publication Data
US 2021/0157278 A1 May 27, 2021

(30) Foreign Application Priority Data
Nov. 26, 2019 (CN) .......................... 201922070114.4

(51) Int. Cl.
*G02F 1/1333* (2006.01)
*G04G 17/04* (2006.01)
(Continued)

(52) U.S. Cl.
CPC ....... *G02F 1/133308* (2013.01); *G04G 17/04* (2013.01); *G06F 1/163* (2013.01); *H05K 1/189* (2013.01)

(58) Field of Classification Search
CPC ............ G02F 1/1333; G02F 1/133308; G02F 1/13338; G04G 1/163; G04G 17/04; G06F 1/163
See application file for complete search history.

(56) References Cited

U.S. PATENT DOCUMENTS

| 2014/0121539 A1 | 5/2014 | Chatterjee et al. |
| 2015/0279589 A1 | 10/2015 | Park |
| 2018/0235542 A1* | 8/2018 | Yun .................. G16H 40/63 |

FOREIGN PATENT DOCUMENTS

| CA | 2340818 A1 | 9/2001 |
| CN | 103006203 A | 4/2013 |
| (Continued) | | |

OTHER PUBLICATIONS

International Search Report for International Application PCT/CN2020/131384 dated Mar. 3, 2021. (5 pages).
(Continued)

*Primary Examiner* — Dung T Nguyen
(74) *Attorney, Agent, or Firm* — Young Basile Hanlon & MacFarlane, P.C.

(57) ABSTRACT

The present disclosure relates to an electronic device and a wearable device with an elastomeric member. The electronic device includes a housing, a key, a circuit board, a trigger structure and the elastomeric member. The key is connected to the housing and movable relative to the housing when pressed. The circuit board is connected to the housing. The trigger structure is electrically connected to the circuit board. The elastomeric member includes a first connection and a second connection, the first connection being electrically connected to the circuit board, the second connection being abutted on the key. The key, the first connection, and the second connection are conductive to the circuit board. When the key is pressed, the elastomeric member is capable of generating two level of deformation and causing the second connection to switch from a state spaced apart from the trigger structure to a state contacting the trigger structure.

20 Claims, 9 Drawing Sheets

(51) Int. Cl.
    *G06F 1/16*    (2006.01)
    *H05K 1/18*    (2006.01)

(56) References Cited

FOREIGN PATENT DOCUMENTS

| | | |
|---|---|---|
| CN | 207136846 U | 3/2018 |
| CN | 108270900 A | 7/2018 |
| CN | 208208619 U | 12/2018 |
| CN | 109634447 A | 4/2019 |
| CN | 109766020 A | 5/2019 |
| CN | 109962533 A | 7/2019 |
| CN | 211294932 U | 8/2020 |
| CN | 211531089 U | 9/2020 |
| EP | 1985231 A1 | 10/2008 |
| EP | 2989965 A2 | 3/2016 |

OTHER PUBLICATIONS

Extended European Search Report for EP Application 20000427.3 dated Mar. 25, 2021. (9 pages).
Indian Examination Report for IN Application 202014051455 dated Jul. 26, 2021. (5 pages).
Invitation pursuant to Rule 137(4) EPC and Article 94(3) EPC for EP Application 20000427.3 dated Sep. 29, 2021. (2 pages).
Communication pursuant to Article 94(3) EPC for EP Application 20000427.3 dated Nov. 16, 2021. (5 pages).

* cited by examiner

ELECTRONIC DEVICE AND WEARABLE DEVICE WITH ELASTOMERIC MEMBER

CROSS-REFERENCE TO RELATED APPLICATION(S)

The present application claims foreign priority to Chinese Patent Applications No. 201922070114.4, field on Nov. 26, 2019, the entire contents of which are hereby incorporated by reference

TECHNICAL FIELD

The present disclosure relates to the field of wearable devices, in particular to an electronic device and a wearable device with an elastomeric member.

BACKGROUND

Wearable devices such as a smart watch may be configured with an electrocardiogram (ECG) sensor. A first measuring electrode of the ECG sensor is usually arranged on a back side of the dial. The crown is configured as a second measuring electrode of the ECG sensor. When the smart watch is worn on an arm of a user, the first measuring electrode is pressed against the skin. When the user touches the crown with another hand, a detection circuit is formed to obtain an ECG data from the user. When the crown is configured as the second measuring electrode, a connection structure between the crown and the ECG sensor is complicated.

SUMMARY

The present disclosure provides an electronic device. The electronic device includes a housing arranged with a mounting cavity and a mounting hole connected to the mounting cavity. The electronic device includes a key disposed in the mounting hole and configured to be movable relative to the housing when the key is pressed. The electronic device includes a circuit board mounted in the mounting cavity. The electronic device includes a trigger structure electrically connected to the circuit board. The electronic device includes an elastomeric member including a first connection and a second connection connected to the first connection. The first connection is electrically connected to the circuit board. The second connection is abutted on the key. The key, the first connection, the second connection are conductive to the circuit board. The electronic device is capable of being worn on a body of a user, and is capable of measuring a biological data of the user through the key when the body of the user is in contact with the key and conductive to the key. When the key is pressed, the elastomeric member is capable of generating two levels of deformation. During a first level of deformation, the first connection is deformed relative to the housing, and the first connection approaches the trigger structure. During a second level of deformation, the second connection is deformed relative to the first connection and switches from a state spaced apart from the trigger structure to a state in contact with the trigger structure.

The present disclosure provides an electronic device. The electronic device includes a housing arranged with a mounting cavity and a mounting hole connected to the mounting cavity. The electronic device includes a key disposed in the mounting hole and configured to be movable relative to the housing when the key is pressed. The electronic device includes a circuit board mounted in the mounting cavity. The electronic device includes a trigger structure electrically connected to the circuit board. The electronic device includes an elastomeric member including a first connection having a first flat top surface and a second connection extending from the first connection. The first connection is electrically connected to the circuit board. The second connection is abutted on the key. The key, the first connection, the second connection are conductive to the circuit board. The electronic device is capable of being worn on a body of a user, and is capable of measuring a biological data of the user through the key when the body of the user is in contact with the key and conductive to the key. The second connection is slightly tilted relative to the first flat top surface. The second connection has two states. When the key is pressed, the second connection is in a first state, and the second connection is connected with the trigger structure. When the key is not pressed, the second connection is in a second state, and the second connection is disconnected with the trigger structure.

The present disclosure provides a wearable device including an electronic device. The electronic device includes a housing arranged with a mounting cavity and a mounting hole connected to the mounting cavity. The electronic device includes a key disposed in the mounting hole and configured to be movable relative to the housing when the key is pressed. The electronic device includes a circuit board mounted in the mounting cavity. The electronic device includes a trigger structure electrically connected to the circuit board. The electronic device includes an elastomeric member including a first connection and a second connection connected to the first connection. The first connection is electrically connected to the circuit board. The second connection is abutted on the key. The key, the first connection, the second connection are conductive to the circuit board. The electronic device is capable of being worn on a body of a user, and is capable of measuring a biological data of the user through the key when the body of the user is in contact with the key and conductive to the key. When the key is pressed, the elastomeric member is capable of generating two levels of deformation. During a first level of deformation, the first connection is deformed relative to the housing, and the first connection approaches the trigger structure. During a second level of deformation, the second connection is deformed relative to the first connection and switches from a state spaced apart from the trigger structure to a state in contact with the trigger structure. The wearable device includes a strap, connected to the housing and configured to allow the electronic device to be worn on the body of the user.

BRIEF DESCRIPTION OF DRAWINGS

To further illustrate technical solutions of embodiments of the present disclosure, drawings needed for description of the embodiments will be briefly introduced. Obviously, the following drawings are only some embodiments of the present disclosure. To any one of skill in the art, other drawings may be obtained without any creative work based on the following drawings.

DETAILED DESCRIPTION

To facilitate the understanding of the present disclosure, the present disclosure will be more fully described with reference to the relevant accompanying drawings. Embodiments of the present disclosure are given in the accompanying drawings. However, the present disclosure may be implemented in many different forms and is not limited to the embodiments described herein. Rather, the provided embodiments are to provide a more thorough and comprehensive understanding of the present disclosure.

Figure 1:
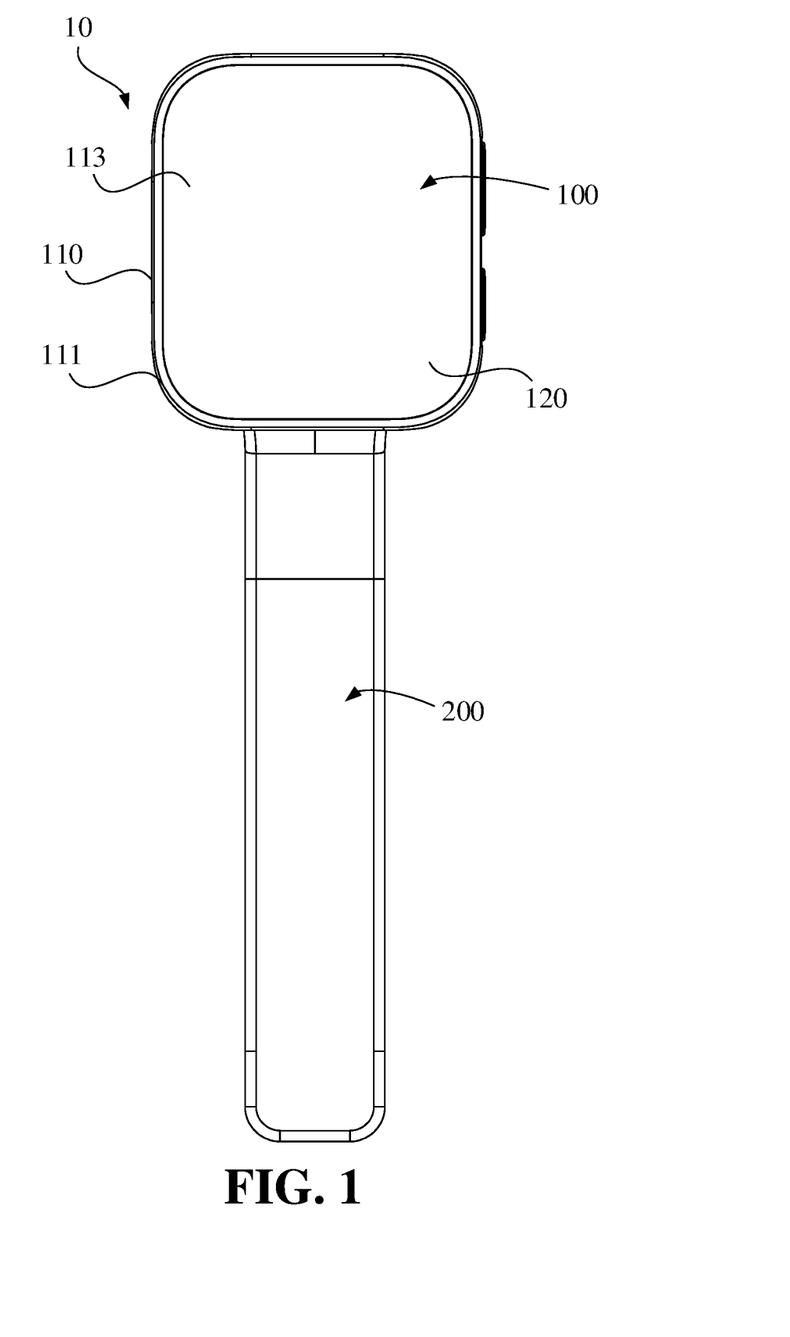
FIG. 1 is a front view of a wearable device according to an embodiment of the present disclosure.
Figure 2:
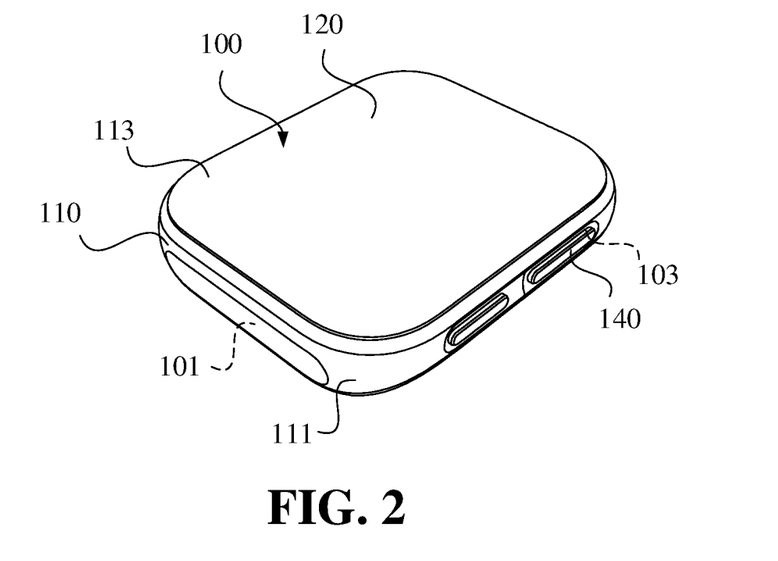
FIG. 2 is a perspective view of an electronic device of the wearable device as illustrated in FIG. 1.
Figure 3:
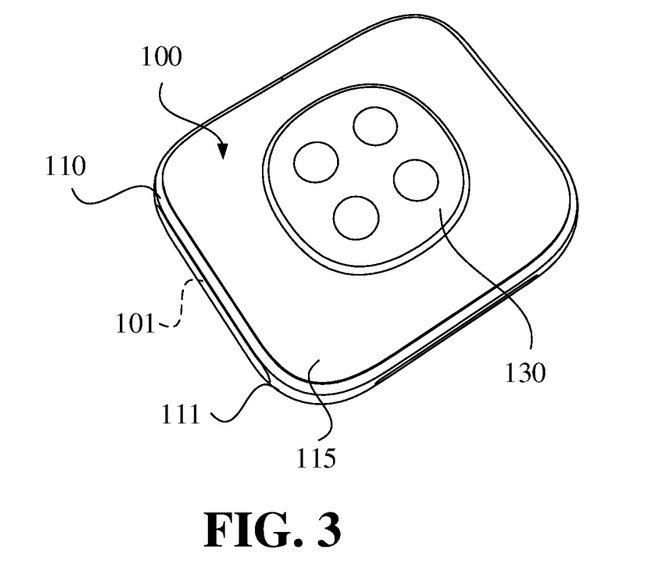
FIG. 3 is a view similar to FIG. 2, but shown from a different aspect.

Referring to FIGS. 1, 2 and 3, a wearable device 10 includes an electronic device 100 and a strap 200. The strap 200 may be disposed at the electronic device 100. The electronic device 100 is wearable on an arm of a user via the strap 200. The electronic device 100 includes a housing 110 and electronic components such as a circuit board 180, a battery, and other electronic components arranged in the housing 110. The housing 110 defines a mounting cavity receiving the circuit board 180, the battery, and the other electronic components. The housing 110 may further include a middle frame 111, a face cover 113 and a rear cover 115. The face cover 113 is arranged at an end of the middle frame 111 and the rear cover 115 is arranged at another end of the middle frame 111 opposite to the face cover 113. The face cover 113 and the rear cover 115 are configured to respectively cover openings at two ends of the mounting cavity. The middle frame 111 may be made of a non-metallic material such as plastic, rubber, silicone, wood, ceramic, or glass, and may also be made of a metallic material such as stainless steel, aluminum, or magnesium alloy. The rear cover 115 may be made of a same or different material as the middle frame 111. In some embodiments, the middle frame 111 and the rear cover 115 are integrally formed, and the face cover 113 is a separate component. The face cover 113 may be made of glass or sapphire, such that a high degree of light transmission may be achieved, and the face cover 113 may be scratch resistant. In some embodiments, the wearable device 10 is a smart watch. The mounting cavity may be configured to receive the battery, the circuit board 180, a display 120, a biosensor 190 such as an ECG sensor, and other electronic components. The circuit board 180 may integrate a processor, a storage unit, a communication module, and other electronic components. The battery may provide power to the circuit board 180, the display 120, and other electronic components. However, the display 120 is not obligatory. In some embodiments in which the display 120 is omitted, the face cover 113 may be omitted, or the face cover 113 may be made of a same material as, and integrated with, the middle frame 111. The biosensor 190 may be configured to detect a biological data such as a heart rate, a respiration rate, a blood pressure, or a body fat. For example, in some embodiments of the present disclosure, the circuit board 180 integrates an electrocardiogram (ECG) sensor for obtaining an ECG data from the user. In some embodiments, the biosensor 190 may also be configured to detect a movement state such as for pacing. In some embodiments, the wearable device 10 may be a sports watch or a conventional watch, a common form of the sports watch being an electronic watch and a common form of the conventional watch being a mechanical watch. In some other embodiments, the wearable device 10 may also be a smart bracelet, etc.

The housing 110 may have a substantially rectangular shape, and four corners of the rectangle may be chamfered to make a rounded transition, such that the wearable device 10 may have a better appearance characteristic. In other embodiments, the housing 110 may also have a substantially rounded shape. The housing 110 may be arranged with a slot 101 on a side to mount the strap 200. In some embodiments, the slot 101 is wholly arranged in the middle frame 111. In other embodiments, the slots 101 is partly arranged in the middle frame 111, and partly in the rear cover 115. Of course, the slot 101 may also extend to the face cover 113 without extending to the rear cover 115. As shown in FIGS. 1 and 2, the strap 200 may have a strip shape, being capable of being mounted to the housing 110 from the slot 101 and forming a reliable connection to the housing 110, such that the electronic device 100 may be reliably worn on the arm of the user. In some embodiments, the strap 200 may also be easily detachable from the housing 110, such that the user may replace the strap 200 easily. In some embodiments, the strap 200 is divided into two segments. The slots 101 are arranged at each end facing back to each other of the electronic device 100 respectively. An end of each segment of the strap 200 is connected to the electronic device 100, and another end of each segment of the strap 200 backed away from the electronic device 100 may be snapped together to define a holding space, such that the wearable device 10 may be worn on the arm of the user via the strap 200. In other embodiments, the strap 200 may be an integral structure, with each end of the strap 200 connected to the electronic device 100 respectively. The strap 200 may be adjusted to a size of the holding space by other structures such as grommets, snaps, elastic expansions, etc., to facilitate wearing by the user. The wearable device 10 according to the present disclosure is illustrated with a two-segment strapping 200 as an example. However, it is understood that the structure in the present disclosure is also applicable to other forms of strap 200.

Referring to FIG. 3, the electronic device 100 includes a detection electrode 130 disposed on the rear cover 115 and exposed on a side of the rear cover 115 away from the face cover 113. The detection electrode 130 is electrically connected to the ECG sensor. When the electronic device 100 is worn on the arm of the user, the detection electrode 130 contacts a skin of the user to detect a biological current on a skin surface. Specifically, in some embodiments, some or all of the rear cover 115 is made of a non-metal such as glass, or ceramic, or a polymeric material. The detection electrode 130 may be a metallic coating disposed on an outer surface of the rear cover 115. The metallic coating may be electroplated or sprayed or printed to be disposed on the outer surface of the rear cover 115. The metallic coating is electrically connected to the ECG sensor. In other embodiments, the detection electrode 130 may be a metal contact disposed on and exposed to the rear cover 115. The metal contact is electrically connected to the ECG sensor, and may be configured with a relatively large contact area to ensure a reliability of the contact of the detection electrode 130 with the skin. Further, in some embodiments, a drive electrode may be arranged on a side of the rear cover 115 facing back to the face cover 113. The drive electrode is electrically connected to the ECG sensor. The drive electrode may be constructed in a form of a metal coating or a metal contact or a metal patch. The drive electrode is isolated from the detection electrode. When the electronic device 100 is worn on the arm of the user, the drive electrode is contacted with the skin of the user and conductive to the user. The drive electrode may enhance an interference resisting ability of an ECG detection circuit to improve the reliability of the ECG measurement. Of course, in other embodiments, the drive electrode may be disposed at other locations of the wearable device 10 such as the strap 200, which will not be repeated herein.

Figure 4:
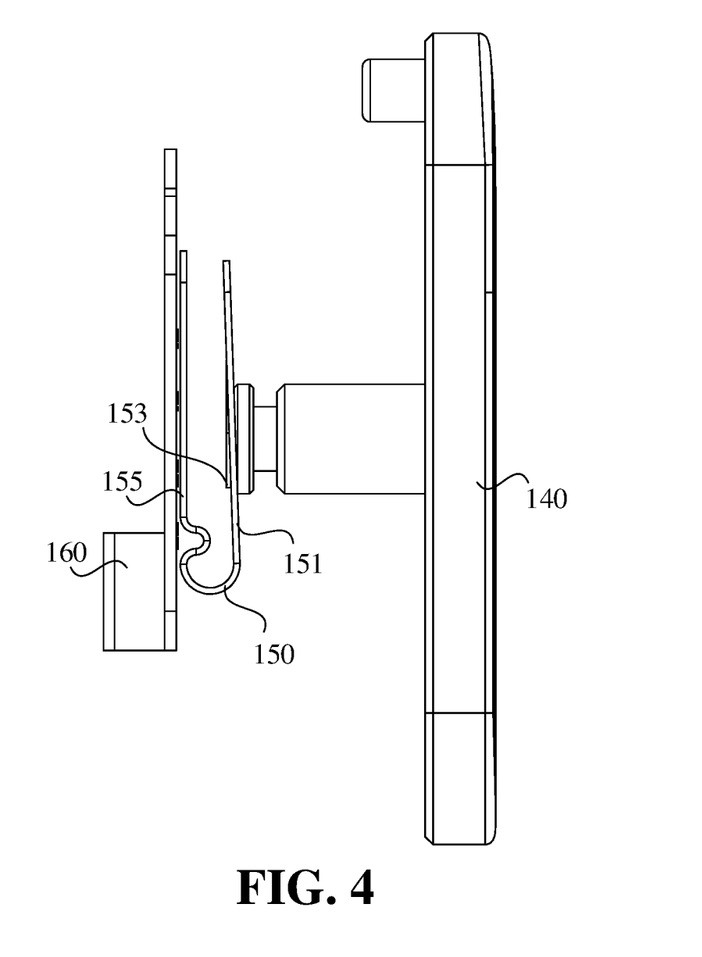
FIG. 4 is a structural schematic view of an assembly of a key, an elastomeric member and a flexible circuit board of the electronic device as illustrated in FIG. 2.
Figure 10:
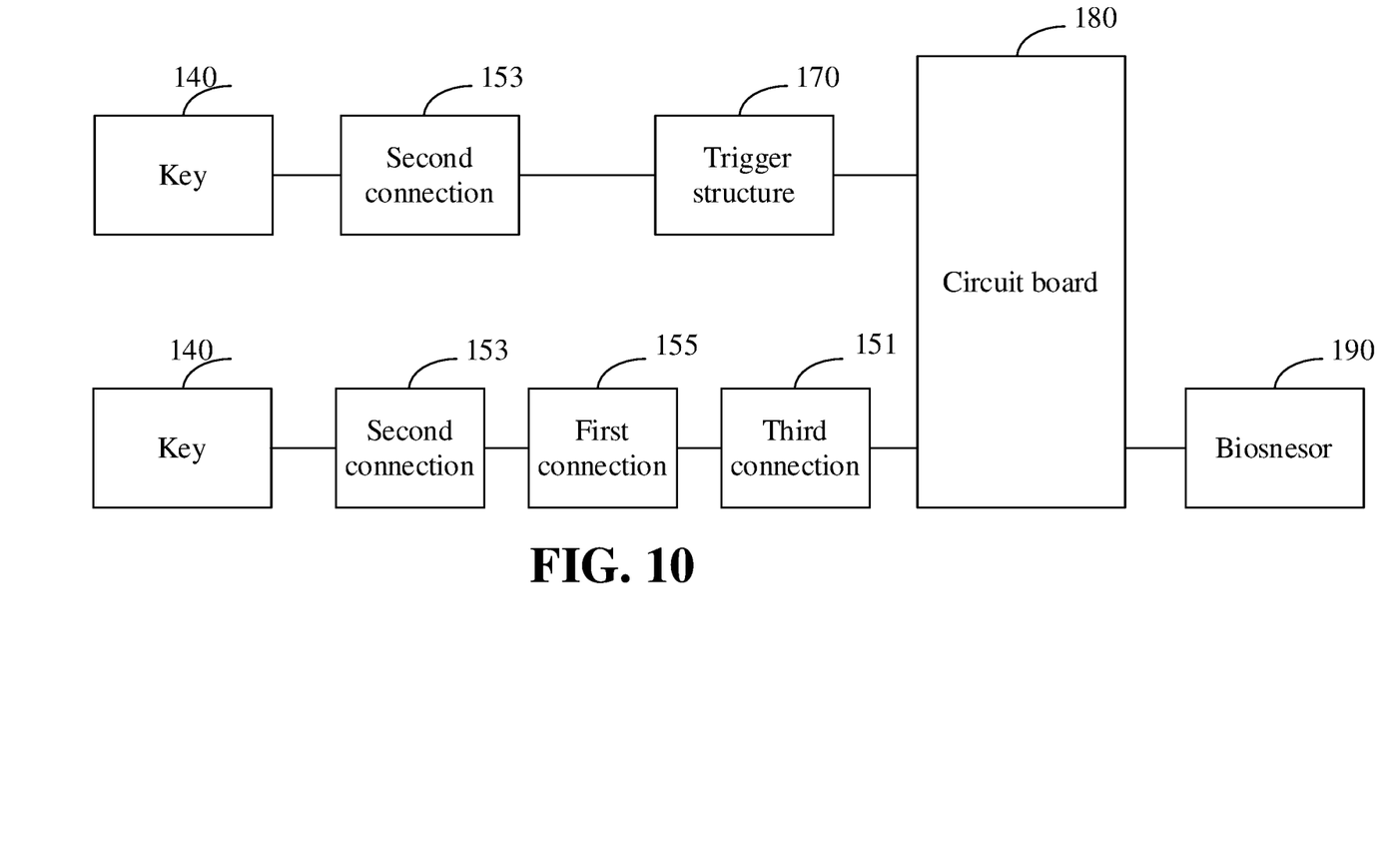
FIG. 10 is a flow chart of performing an input function through a trigger structure, and performing measuring a biological data by a biosensor.

Referring to FIGS. 2 and 4, the electronic device 100 includes a key 140, a trigger structure 170, and an elastomeric member 150 for performing an input function. The middle frame 111 is arranged with a mounting hole 103 connected to the mounting cavity. The key 140 is disposed at the mounting hole 103 and configured to be movable relative to the housing 110 when pressed. The key 140 is a mechanical press structure. The elastomeric member 150 is connected to the housing 110 or the circuit board 180. The trigger structure 170 is connected to the housing 110 or the circuit board 180, and is electrically connected to the circuit board 180. Further referring to FIG. 10, when the key 140 is pressed, the key 140 moves into the mounting cavity and drives the elastomeric element 150 to deform until the key 140 or the elastomeric element 150 presses against the trigger structure 170, thereby executing the input function of the key 140. For example, the key 140 may be pressed to adjust the volume of the electronic device 100, or perform a lock or an unlock function, or perform a selection function. Specifically, the trigger structure 170 may be a metal contact structure, or other circuitry structures. In some embodiments, when the key 140 is pressed, a portion of the key 140 is pressed against the trigger structure 170 to perform the input function. In other embodiments, at least a portion of the structure of the elastomeric member 150 is positioned between the trigger structure 170 and the key 140. When the key 140 is pressed, the key 140 drives the elastomeric member 150 to deform and press against the trigger structure 170, thereby performing the input function. The elastomeric member 150 is configured to accumulate an elastic potential energy during being pressed. When the key 140 is no longer pressed, the elastomeric member 150 may release the elastic potential energy to return the key 140 to an initial position for a next press.

Figure 5:
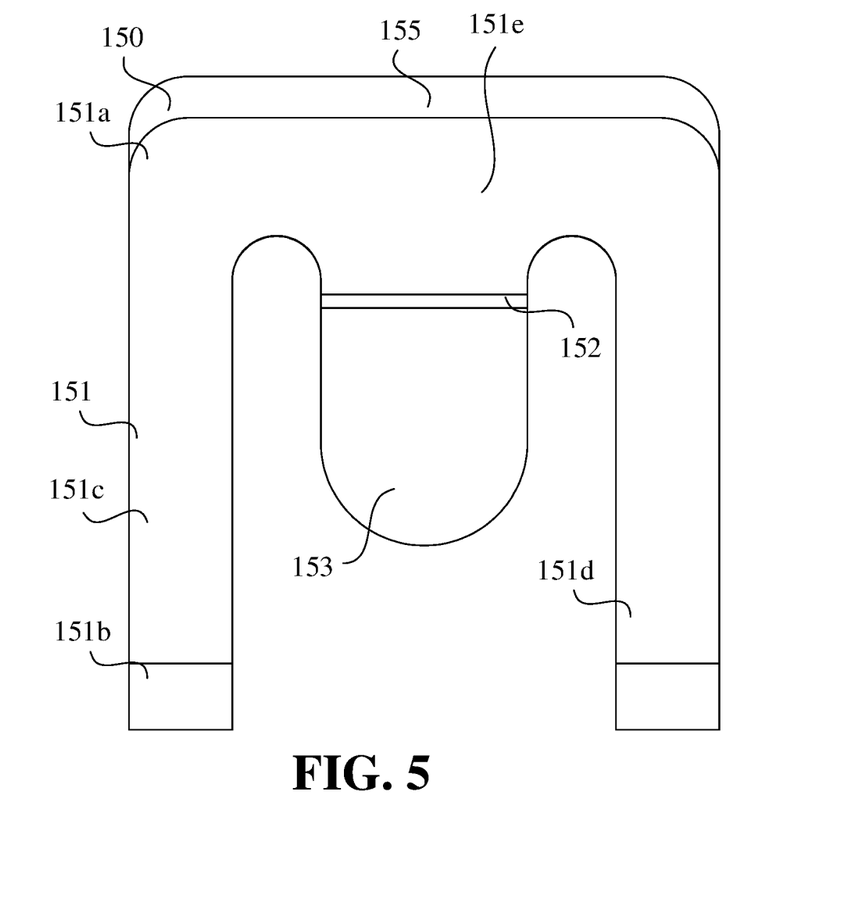
FIG. 5 is a front view of the elastomeric member of the electronic device as illustrated in FIG. 4.
Figure 6:
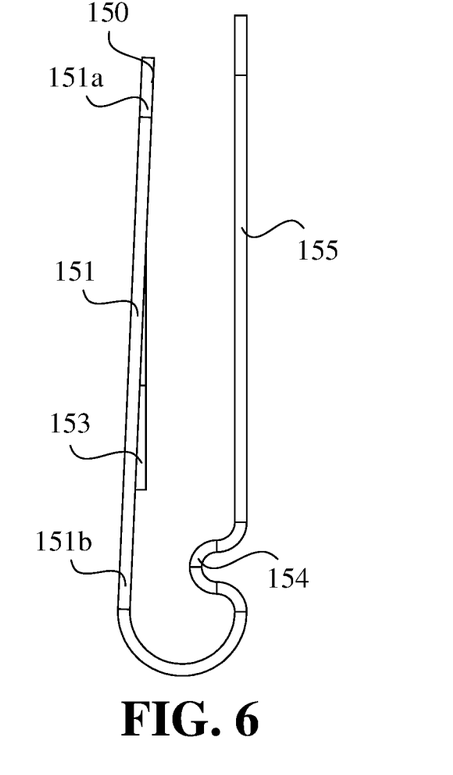
FIG. 6 is a right view of the elastomeric member of the electronic device as illustrated in FIG. 5.
Figure 7:
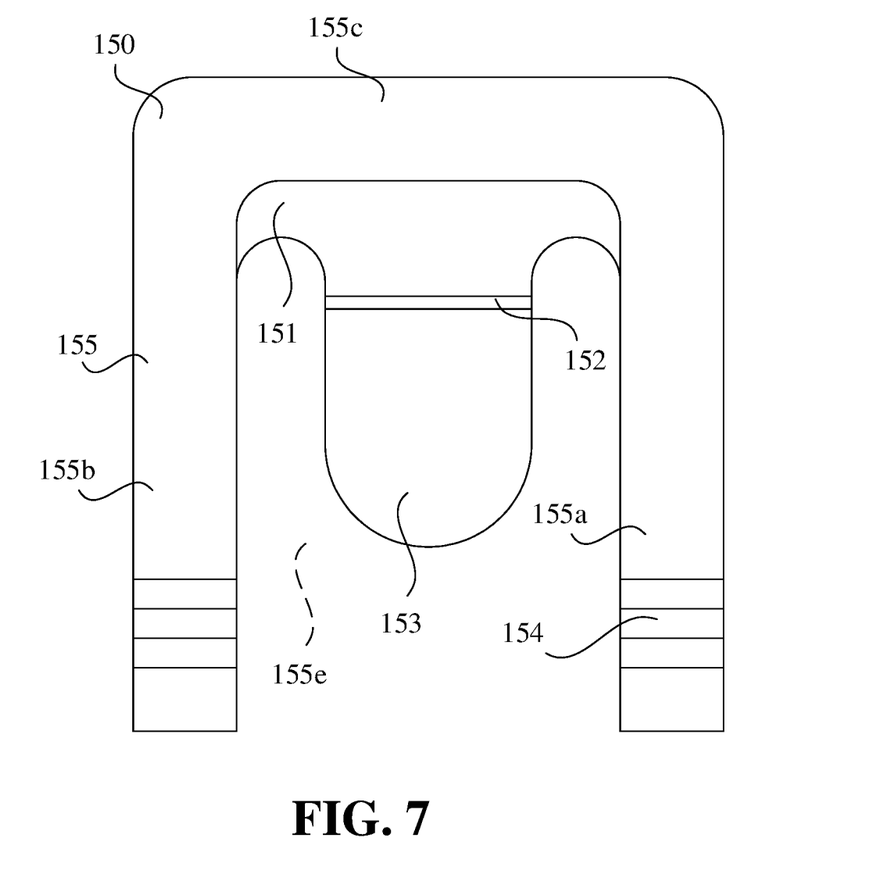
FIG. 7 is a rear view of the elastomeric member of the electronic device as illustrated in FIG. 5.

Referring to FIGS. 5, 6, and 7, the elastomeric member 150 may be in a form of a thin sheet, and may be stamped from a sheet of metal. The elastomeric member 150 electrically connects the key 140 to the ECG sensor and maintains a conduction therebetween. In some embodiments, the key 140 is made of a metal. The key 140 is electrically connected to the ECG sensor via the elastomeric member 150, such that the key 140 is configured as another detection electrode for the ECG sensor. Of course, in other embodiments, the key 140 may include a substrate and a metal layer, the substrate being made of a non-metal such as plastic, ceramic, glass, etc., and a surface of the substrate being coated with a metal layer. The metal layer on the surface of the substrate is exposed to the housing 110 and electrically connected to the ECG sensor, and may be configured as another detection electrode of the ECG sensor.

Referring to FIG. 5, the elastomeric member 150 includes a first connection 151 and a second connection 153 connected to the first connection 151. The first connection 151 is electrically connected to the circuit board 180. The second connection 153 is abutted on the key 140. As shown in FIG. 4, the key 140, the second connection 153, and the first connection 151 are conductive to the ECG sensor. The electronic device 100 may be worn on the arm of the user, and the detection electrode 130 is thus contacted with the skin of the user. Further referring to FIG. 10, when the other hand of the user touches the key 140, the key 140, the elastomeric member 150, the ECG sensor, and the detection electrode 130 form a detection circuit with the body of the user to obtain the ECG data of the user. Of course, the ECG detection circuit may include other circuit components. When the key 140 is pressed, the elastomeric member 150 may generate two levels of deformation. In a first level of deformation, the first connection 151 is deformed relative to the housing 110 and approaches the trigger structure 170. In a second level of deformation, the second connection 153 is deformed relative to the first connection 151 and switches from a state spaced apart from the trigger structure 170 to a state in contact with the trigger structure 170. It is understood that the two levels of deformation of the elastomeric member 150 may be generated simultaneously or with a time difference. In both cases, the two levels of deformation may be simplified: during the first level of deformation, the first connection 151 is deformed and approaches the trigger structure 170, and the second connection 153 is not deformed relative to the first connection 151; during the second level of deformation, the second connection 153 is deformed relative to the first connection 151 and able to be abutted on the trigger structure 170, and the first connection 151 is not deformed.

The electronic device 100, after being worn on the arm of the user to connect the detection electrode 130 with the skin of the user, the other hand of the user may touch the key 140. In this way, the key 140, the elastomeric member 150, the ECG sensor, and the detection electrode 130 may form the detection circuit with the body of the user, thereby obtaining the ECG data of the user. Since the key 140 is multiplexed as a measuring electrode of the ECG sensor, and the elastomeric member 150 may keep the key 140 and the ECG sensor conductive, the key 140 and the ECG sensor thus form a relatively simple and highly reliable electrical connection structure. In the process of pressing the key 140, since the key 140 is capable of generating the two levels of deformation, a deformation value of each level of the deformation is relatively small when the key 140 is subjected to a same pressing force compared to the case of single level of deformation, thereby increasing a fatigue life of the elastomeric member 150 and thus increasing a service life of the key 140.

Of course, the deformation of the elastomeric member 150 may be described from another perspective. When the key 140 is pressed, the key 140 is able to apply a torque in a first direction to the first connection 151, such that an end of the first connection 151 moves closer to the trigger structure 170. The key 140 is also able to apply a torque in a second direction to the second connection 153, such that the second connection 153 is deformed relative to the first connection 151. The first direction is opposite to the second direction. The second connection 153 switches from a state spaced apart from the trigger structure 170 to a state in contact with the trigger structure 170. For example, in some embodiments as shown in FIG. 6, when the key 140 is pressed, the key 140 applies a clockwise torque to the first connection 151, such that an end of the first connection 151 moves closer to the trigger structure 170. The key 140 applies a counterclockwise torque to the second connection 153, such that the second connection 153 is deformed relative to the first connection 151 to be abutted on the trigger structure 170. Further, the first connection 151 and the second connection 153 may be arranged with a cushioning structure to guide the deformation. Specifically, referring to FIG. 5, a first bending region 152 is arranged at a connection position of the second connection 153 and the first connection 151. The first bending region 152 may be formed by stamping and formed in a groove shape, such that the deformation of the first connection 151 may be more concentrated at the first bending region 152. The first bending region 152 may improve the fatigue life of the elastomeric member 150 and thus the service life of the key 140.

Of course, the deformation of the elastomeric member 150 may be described from another perspective. Referring to FIGS. 5 and 6, the first connection 151 of the elastomeric member 150 includes a first end 151a and a second end 151b opposite to the first end 151a. The first end 151a is a free end and capable of being driven to move relative to the housing 110 when the key 140 is pressed. The second connection 153 is connected to the first end 151a and wholly disposed at a side of the first end 151a facing the second end 151b. The second connection 153 is abutted on the key 140. The key 140, the second connection 153, and the first connection 151 are conductive to the ECG sensor. Specifically, while the key 140 is pressed, the key 140 is capable of driving the first end 151a of the first connection 151 to be offset relative to the second end 151b and move closer to the trigger structure 170. The key 140 is capable of driving the second connection 153 to be offset relative to the first end 151a. In the embodiments, since the second connection 153 is connected to the first end 151a and wholly disposed at a side of the first end 151a facing the second end 151b, an overlapping area may exist between the second connection 153 and the first connection 151 in a length extending direction of the first connection 151, thereby reducing an overall length of the elastomeric member 150. In some embodiments, the length direction of the elastomeric member 150 extends in a thickness direction of the electronic device 100. The structure of the elastomeric member 150 facilitates a thin and light design of the electronic device 100.

Figure 8:
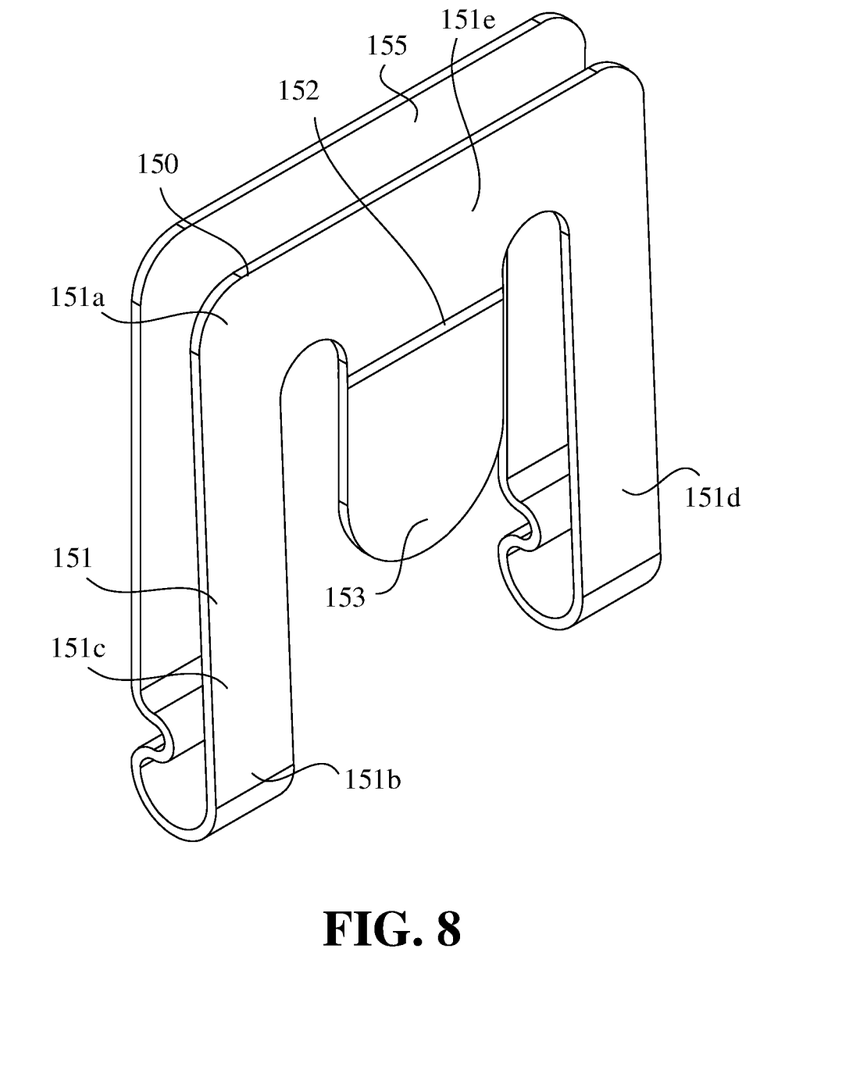
FIG. 8 is a perspective view of the elastomeric member of the electronic device as illustrated in FIG. 5.
Figure 9:
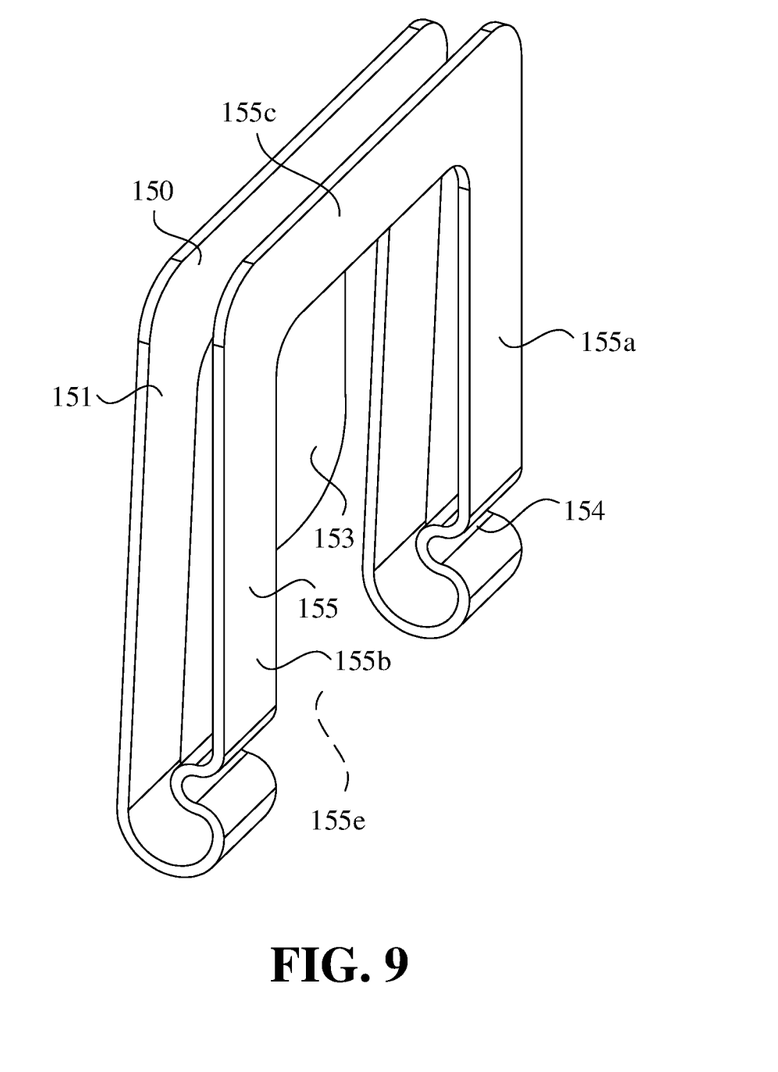
FIG. 9 is a view similar to FIG. 8, but shown from a different aspect.

Further, referring to FIGS. 8 and 9, the elastomeric member 150 may have a substantially U shape. The elastomeric member 150 includes a third connection 155 connected to the first connection 151. The key 140 and the second connection 153 are disposed on a same side as the third connection 155. The third connection 155 is superimposed on and spaced from the first connection 151. Specifically, referring to FIG. 6, the third connection 155 is connected to the second end 151b of the first connection 151. The second connection 153 is arranged with a second bending region 154. The second bending region 154 is disposed at a connection position between the first connection 151 and the third connection 155, i.e., the second bending region 154 is disposed close to the second end 151b. The second bending region 154 may be formed using a stamping method to form a groove, such that the deformation of the first connection 151 may be more concentrated at the second bending region 154. The second bending region 154 may also enhance the fatigue life of the elastomeric member 150, and thus the life of the key 140. Of course, the second bending region 154 may be disposed at the first connection 151. Of course, the number of the second bending regions 154 may be two or more, with at least one second bending region 154 disposed at the first connection 151 and other second bending regions 154 disposed at the third connection 155. In some embodiments, each of the first connection and the third connection has an even and same thickness The third connection 155 may be electrically connected to the circuit board 180, supported by the circuit board 180, and electrically connect the elastomeric member 150 to the ECG sensor. Further, referring to FIG. 4, the electronic device 100 includes a flexible circuit board 160 disposed on a side of the third connection 155 backed away from the second connection 153. The flexible circuit board 160 electrically connects the third connection 155 to the ECG sensor. The flexible circuit board 160 may be reliably connected to the third connection 155 via a surface mounted technology (SMT) process. Of course, in other embodiments, the third connection 155 may be omitted. In embodiments in which the third connection 155 is omitted, the second connection 153 may be electrically connected to the circuit board 180. The second connection 153 may be connected to the housing 110, supported by the housing 110, and deformed relative to the housing 110 when the key 140 is pressed.

Further, referring to FIG. 5, the first connection 151 may have a substantially U shape. The first connection 151 includes a first arm 151c, a second arm 151d, and a first connection arm 151e connected between the first arm 151c and second arm 151d. The first arm 151c, the second arm 151d, and the first connection arm 151e are spaced apart from each other. The second connection 153 is connected to the first connection arm 151e and is disposed between the first arm 151c and second arm 151d. The third connection 155 is connected to an end of the first arm 151c and an end of the second arm 151d away from the first connection arm 151e. Further, referring to FIG. 7, the third connection 155 may have a substantially U shape. The third connection 155 includes a third arm 155a, a fourth arm 155b, and a second connection arm 155c. An end of the third arm 155a is connected to the first arm 151c, and another end of the third arm 155a is connected to an end of the second connection arm 155c. An end of the fourth arm 155b is connected to the second arm 151d and another end of the fourth arm 155b is connected to another end of the second connection arm 155c. The third arm 155a, the second connecting arm 155c and the fourth arm 155b define a skeletonized area 155e. At least a part of the trigger structure 170 is disposed at the skeletonized area 155e and capable of contacting the second connection part 153 when the key 140 is pressed.

The technical features of each of the above-described embodiments can be combined in any number of ways. All possible combinations of the technical features of each of the above-mentioned embodiments have not been described in order to keep the description concise. However, as long as there is no contradiction in the combinations of these technical features, they should be considered to be within the scope of the present disclosure.

The above-mentioned embodiments only describe several ways of implementation of the present disclosure, which are described in a more specific and detailed manner, but should not be construed as a limitation on the scope of the present disclosure. It should be noted that, for those of ordinary skill in the art, a number of deformations and improvements can be made without departing from the idea of the present disclosure, which are within the scope of the present disclosure. Therefore, the scope of the present disclosure shall be governed by the appended claims.

What is claimed is:

1. An electronic device, comprising:
a housing, arranged with a mounting cavity and a mounting hole connected to the mounting cavity;
a key, disposed in the mounting hole and configured to be movable relative to the housing when the key is pressed;
a circuit board, mounted in the mounting cavity;
a trigger structure, electrically connected to the circuit board; and
an elastomeric member comprising a first connection and a second connection connected to the first connection, wherein the first connection is electrically connected to the circuit board; the second connection is abutted on the key; the key, the first connection, and the second connection are conductive to the circuit board; the electronic device is capable of being worn on a body of a user, and is capable of measuring a biological data of the user through the key when the body of the user is in contact with the key and conductive to the key;
wherein when the key is pressed, the elastomeric member is capable of generating two levels of deformation; during a first level of deformation, the first connection is deformed relative to the housing, and the first connection approaches the trigger structure; and during a second level of deformation, the second connection is deformed relative to the first connection and switches from a state spaced apart from the trigger structure to a state in contact with the trigger structure.

2. The electronic device according to claim 1, wherein the elastomeric member comprises a third connection connected to the first connection; the key and the second connection are disposed on a same side of the third connection; the third connection is superimposed on the first connection and forms a spacing with the first connection; and the third connection is capable of being electrically connected to the circuit board, supported by the circuit board, and electrically connect the elastomeric member to a biosensor.

3. The electronic device according to claim 2, wherein the first connection comprises a first arm, a second arm, and a first connection arm connected between the first arm and the second arm; the first arm, the second arm, and the first connection arm are spaced apart from each other; and the second connection is connected to the first connection arm and disposed between the first arm and the second arm, and the third connection is connected to an end of the first arm away from the first connection arm and an end of the second arm away from the first connection arm.

4. The electronic device according to claim 3, wherein the third connection comprises a third arm, a fourth arm and a second connection arm; an end of the third arm is connected to the first arm, and another end of the third arm is connected to an end of the second connection arm; an end of the fourth arm is connected to the second arm, and another end of the fourth arm is connected to another end of the second connection arm; the third arm, the second connecting arm and the fourth arm define a skeletonized area; and at least a part of the trigger structure is disposed at the skeletonized area and capable of contacting the second connection part when the key is pressed.

5. The electronic device according to claim 2, wherein a first bending region is arranged at a connection position of the second connection and the first connection; and at a position close to a connection position of the first connection and the third connection, the first connection or the third connection is arranged with a second bending region.

6. The electronic device according to claim 2, wherein the electronic device comprises a flexible circuit board disposed on a side of the third connection backed away from the second connection, the flexible circuit board electrically connecting the third connection to the circuit board.

7. The electronic device according to claim 1, wherein the key is a metal key; or, the key comprises a substrate and a metal layer disposed on a surface of the substrate, the metal layer being exposed to the housing and conductive to the second connection.

8. The electronic device according to claim 1, wherein the housing comprises a middle frame, a rear cover and a face cover; the face cover is arranged at an end of the middle frame and the rear cover is arranged at another end of the middle frame opposite to the face cover; the face cover, the rear cover and the middle frame define a mounting cavity; the circuit board is mounted in the mounting cavity; and a detection electrode is disposed on the rear cover and exposed on a side of the rear cover, wherein the detection electrode is electrically connected to the biosensor.

9. An electronic device, comprising:
a housing, arranged with a mounting cavity and a mounting hole connected to the mounting cavity;
a key, disposed in the mounting hole and configured to be movable relative to the housing when the key is pressed;
a circuit board, mounted in the mounting cavity;
a trigger structure, electrically connected to the circuit board; and
an elastomeric member comprising a first connection having a first flat top surface and a second connection extending from the first connection, wherein the first connection is electrically connected to the circuit board; the second connection is abutted on the key; the key, the first connection, and the second connection are conductive to the circuit board; the electronic device is capable of being worn on a body of a user, and is capable of measuring a biological data of the user through the key when the body of the user is in contact with the key and conductive to the key;
wherein the second connection is capable of being slightly tilted relative to the first flat top surface; the second connection has two states; when the key is pressed, the second connection is in a first state, and the second connection is connected with the trigger structure; and when the key is not pressed, the second connection is in a second state, and the second connection is disconnected with the trigger structure.

10. The electronic device according to claim 9, wherein the elastomeric member comprises a third connection connecting with the first connection and having a second flat top surface; wherein a distance between the first flat top surface and the second flat top surface is gradually decreased along a direction from a connection position at which the first connection and the third connection are connected to an open end at which the first connection and the third connection are disconnected; and the third connection is capable of being electrically connected to the circuit board, supported by the circuit board, and electrically connect the elastomeric member to a biosensor.

11. The electronic device according to claim 10, wherein each of the first connection and the third connection has an even and same thickness.

12. The electronic device according to claim 10, wherein the first connection comprises a first arm, a second arm, and a first connection arm, wherein the first arm and the second arm are perpendicularly extending from two opposite ends of the first connection arm; the second connection slantwise extends from a central portion of the first connection arm; the second connection is located between the first arm and the second arm; and a length of the second connection is smaller than a length of the first arm or the second arm.

13. The electronic device according to claim 12, wherein at a position close to a connection position of the first connection and the third connection, the first connection or the third connection is arranged with a second bending region; and the second bending region is bent toward the first arm or the second arm correspondingly.

14. The electronic device according to claim 10, wherein the third connection comprises a third arm, a fourth arm, and a second connection arm, wherein the third arm and the fourth arm are perpendicularly extending from two opposite ends of the second connection arm; an end of the third arm is connected to the first arm, and another end of the third arm is connected to an end of the second connection arm; an end of the fourth arm is connected to the second arm, and another end of the fourth arm is connected to another end of the second connection arm; the third arm, the second connecting arm and the fourth arm define a skeletonized area; and at least a part of the trigger structure is disposed at the skeletonized area and capable of contacting the second connection part when the key is pressed.

15. The electronic device according to claim 10, wherein the electronic device comprises a flexible circuit board disposed on a side of the third connection backed away from the second connection, the flexible circuit board electrically connecting the third connection to the circuit board.

16. The electronic device according to claim 9, wherein a first bending region is arranged at a connection position of the second connection and the first connection.

17. The electronic device according to claim 9, wherein the key is a metal key; or, the key comprises a substrate and a metal layer disposed on a surface of the substrate, the metal layer being exposed to the housing and conductive to the second connection.

18. The electronic device according to claim 9, wherein the housing comprises a middle frame, a rear cover and a face cover; the face cover is arranged at an end of the middle frame and the rear cover is arranged at another end of the middle frame opposite to the face cover; the face cover, the rear cover and the middle frame define a mounting cavity; the circuit board is mounted in the mounting cavity; and a detection electrode is disposed on the rear cover and exposed on a side of the rear cover, wherein the detection electrode is electrically connected to the biosensor.

19. A wearable device, comprising:
an electronic device comprising:
a housing, arranged with a mounting cavity and a mounting hole connected to the mounting cavity;
a key, disposed in the mounting hole and configured to be movable relative to the housing when the key is pressed;
a circuit board, mounted in the mounting cavity;
a trigger structure, electrically connected to the circuit board; and
an elastomeric member comprising a first connection and a second connection connected to the first connection, wherein the first connection is electrically connected to the circuit board; the second connection is abutted on the key; the key, the first connection, and the second connection are conductive to the circuit board; the electronic device is capable of being worn on a body of a user, and is capable of measuring a biological data of the user through the key when the body of the user is in contact with the key and conductive to the key;
wherein when the key is pressed, the elastomeric member is capable of generating two levels of deformation; during a first level of deformation, the first connection is deformed relative to the housing, and the first connection approaches the trigger structure; and during a second level of deformation, the second connection is deformed relative to the first connection and switches from a state spaced apart from the trigger structure to a state in contact with the trigger structure; and
a strap, connected to the housing and configured to allow the electronic device to be worn on the body of the user.

20. The wearable device according to claim 19, wherein the elastomeric member comprises a third connection connected to the first connection; the key, the second connection are disposed on a same side of the third connection; the third connection is superimposed on the first connection and forms a spacing with the first connection; and the third connection is capable of being electrically connected to the circuit board, supported by the circuit board, and electrically connect the elastomeric member to the biosensor.

\* \* \* \* \*